US011448656B2

(12) United States Patent
Iovanna et al.

(10) Patent No.: US 11,448,656 B2
(45) Date of Patent: *Sep. 20, 2022

(54) COMPOSITIONS USEFUL IN THE DIAGNOSTIC OF LATENTLY INFECTED *MYCOBACTERIUM TUBERCULOSIS*

(71) Applicants: CENTRE NATIONAL DE LA RECHERCHE SCIENTIFIQUE (C.N.R.S.), Paris (FR); CONICET (CONSEJO NACIONAL DE INVESTIGACIONES CIENTIFICAS Y TECNICAS), Buenos Aires (AR); INSTITUT JEAN PAOLI & IRENE CALMETTES, Marseilles (FR); UNIVERSITÉ D'AIX-MARSEILLE, Marseilles (FR); INSTITUT NATIONAL DE LA SANTE ET DE LA RECHERCHE MEDICALE (INSERM), Paris (FR)

(72) Inventors: Juan Iovanna, Marseilles (FR); Virginia Pasquinelli, Buenos Aires (AR); Maria Madgalena Gherardi, Buenos Aires (AR); Hector Eduardo Chuluyan, Buenos Aires (AR); Ana Inès Rovetta, Buenos Aires (AR); Delfina Pena, Buenos Aires (AR); Véronica Edith Garcia, Buenos Aires (AR)

(73) Assignees: CNRS, Paris (FR); CONICET, Buenos Aires (AR); INSTITUT JEAN PAOLI & IRENE CALMETES, Marseilles (FR); UNIVERSITE D' AIX-MARSEILLE, Marseilles (FR); INSERM, Paris (FR)

(*) Notice: Subject to any disclaimer, the term of this patent is extended or adjusted under 35 U.S.C. 154(b) by 95 days.

This patent is subject to a terminal disclaimer.

(21) Appl. No.: 16/037,150

(22) Filed: Jul. 17, 2018

(65) Prior Publication Data

US 2018/0328948 A1 Nov. 15, 2018

Related U.S. Application Data

(63) Continuation of application No. 15/505,292, filed as application No. PCT/EP2015/069791 on Aug. 28, 2015, now Pat. No. 10,067,147.

(30) Foreign Application Priority Data

Aug. 29, 2014 (EP) .................................. 14306329.5

(51) Int. Cl.
*G01N 33/569* (2006.01)
*C07K 14/35* (2006.01)
*G01N 33/68* (2006.01)
*C12N 5/078* (2010.01)

(52) U.S. Cl.
CPC ......... *G01N 33/6893* (2013.01); *C07K 14/35* (2013.01); *C12N 5/0634* (2013.01); *G01N 33/5695* (2013.01); *G01N 2333/35* (2013.01); *G01N 2333/57* (2013.01)

(58) Field of Classification Search
CPC ............... C07K 14/35; G01N 2333/35; G01N 33/5695; G01N 2333/57; G01N 33/6848; G01N 33/6893; A61K 39/04; C12N 5/0634
See application file for complete search history.

(56) References Cited

U.S. PATENT DOCUMENTS

| | | | |
|---|---|---|---|
| 10,067,147 B2* | 9/2018 | Iovanna | G01N 33/5695 |
| 2007/0026473 A1 | 2/2007 | Gennaro | |
| 2011/0236411 A1* | 9/2011 | Scholler | A61K 39/0011 424/193.1 |

FOREIGN PATENT DOCUMENTS

| | | |
|---|---|---|
| CN | 103360480 A | 10/2013 |
| WO | 2009/039854 A2 | 4/2009 |

OTHER PUBLICATIONS

Butera et al. BMC Infect. Dis. 9: 182, 1-8, 2009.*
Goletti et al. Eur. Respiratory J. 36: 135-142, 2009.*
Pena et al. EBioMedicine 2: 884-890, available online May 30, 2015.*

* cited by examiner

*Primary Examiner* — Sarvamangala Devi
(74) *Attorney, Agent, or Firm* — WC&F IP (57) ABSTRACT

The present invention concerns a composition comprising at least three peptides derived from *Mycobacterium tuberculosis* antigen Rv2626c, its use in the diagnostic of latently infected *Mycobacterium tuberculosis* (LTBI) subjects, corresponding methods of use and kits.

2 Claims, 3 Drawing Sheets

Specification includes a Sequence Listing.

SEQUENCE LISTING

<160> NUMBER OF SEQ ID NOS: 42

<210> SEQ ID NO 1
<211> LENGTH: 143
<212> TYPE: PRT
<213> ORGANISM: Mycobacterium tuberculosis

<400> SEQUENCE: 1

Met Thr Thr Ala Arg Asp Ile Met Asn Ala Gly Val Thr Cys Val Gly
1               5                   10                  15

Glu His Glu Thr Leu Thr Ala Ala Gln Tyr Met Arg Glu His Asp
            20                  25                  30

Ile Gly Ala Leu Pro Ile Cys Gly Asp Asp Arg Leu His Gly Met
        35                  40                  45

Leu Thr Asp Arg Asp Ile Val Ile Lys Gly Leu Ala Ala Gly Leu Asp
    50                  55                  60

Pro Asn Thr Ala Thr Ala Gly Glu Leu Ala Arg Asp Ser Ile Tyr Tyr
65                  70                  75                  80

Val Asp Ala Asn Ala Ser Ile Gln Glu Met Leu Asn Val Met Glu Glu
                85                  90                  95

His Gln Val Arg Arg Val Pro Val Ile Ser Glu His Arg Leu Val Gly
                100                 105                 110

Ile Val Thr Glu Ala Asp Ile Ala Arg His Leu Pro Glu His Ala Ile
            115                 120                 125

Val Gln Phe Val Lys Ala Ile Cys Ser Pro Met Ala Leu Ala Ser
    130                 135                 140

<210> SEQ ID NO 2
<211> LENGTH: 15
<212> TYPE: PRT
<213> ORGANISM: Mycobacterium tuberculosis

<400> SEQUENCE: 2

Glu Thr Leu Thr Ala Ala Gln Tyr Met Arg Glu His Asp Ile
1               5                   10                  15

<210> SEQ ID NO 3
<211> LENGTH: 15
<212> TYPE: PRT
<213> ORGANISM: Mycobacterium tuberculosis

<400> SEQUENCE: 3

Asp Asp Arg Leu His Gly Met Leu Thr Asp Arg Asp Ile Val Ile
1               5                   10                  15

<210> SEQ ID NO 4
<211> LENGTH: 15
<212> TYPE: PRT
<213> ORGANISM: Mycobacterium tuberculosis

<400> SEQUENCE: 4

Asp Pro Asn Thr Ala Thr Ala Gly Glu Leu Ala Arg Asp Ser Ile
1               5                   10                  15

<210> SEQ ID NO 5
<211> LENGTH: 14
<212> TYPE: PRT
<213> ORGANISM: Mycobacterium tuberculosis

<400> SEQUENCE: 5

Asn Ala Ser Ile Gln Glu Met Leu Asn Val Met Glu Glu His

<210> SEQ ID NO 6
<211> LENGTH: 15
<212> TYPE: PRT
<213> ORGANISM: Mycobacterium tuberculosis

<400> SEQUENCE: 6

Glu His Arg Leu Val Gly Ile Val Thr Glu Ala Asp Ile Ala Arg
1               5                   10                  15

<210> SEQ ID NO 7
<211> LENGTH: 15
<212> TYPE: PRT
<213> ORGANISM: Mycobacterium tuberculosis

<400> SEQUENCE: 7

Val Gln Phe Val Lys Ala Ile Cys Ser Pro Met Ala Leu Ala Ser
1               5                   10                  15

<210> SEQ ID NO 8
<211> LENGTH: 14
<212> TYPE: PRT
<213> ORGANISM: Mycobacterium tuberculosis

<400> SEQUENCE: 8

Ala Ala Ala Gln Tyr Met Arg Glu His Asp Ile Gly Ala Leu
1               5                   10

<210> SEQ ID NO 9
<211> LENGTH: 14
<212> TYPE: PRT
<213> ORGANISM: Mycobacterium tuberculosis

<400> SEQUENCE: 9

Ala Gln Tyr Met Arg Glu His Asp Ile Gly Ala Leu Pro Ile
1               5                   10

<210> SEQ ID NO 10
<211> LENGTH: 17
<212> TYPE: PRT
<213> ORGANISM: Mycobacterium tuberculosis

<400> SEQUENCE: 10

Met Arg Glu His Asp Ile Gly Ala Leu Pro Ile Cys Gly Asp Asp Asp
1               5                   10                  15

Arg

<210> SEQ ID NO 11
<211> LENGTH: 15
<212> TYPE: PRT
<213> ORGANISM: Mycobacterium tuberculosis

<400> SEQUENCE: 11

Gly Ala Leu Pro Ile Cys Gly Asp Asp Asp Arg Leu His Gly Met
1               5                   10                  15

<210> SEQ ID NO 12
<211> LENGTH: 15
<212> TYPE: PRT
<213> ORGANISM: Mycobacterium tuberculosis

<400> SEQUENCE: 12

Ile Cys Gly Asp Asp Asp Arg Leu His Gly Met Leu Thr Asp Arg

```
                1               5                   10                  15
```

<210> SEQ ID NO 13
<211> LENGTH: 14
<212> TYPE: PRT
<213> ORGANISM: Mycobacterium tuberculosis

<400> SEQUENCE: 13

```
Ala Thr Ala Gly Glu Leu Ala Arg Asp Ser Ile Tyr Tyr Val
1               5                   10
```

<210> SEQ ID NO 14
<211> LENGTH: 15
<212> TYPE: PRT
<213> ORGANISM: Mycobacterium tuberculosis

<400> SEQUENCE: 14

```
Gly Glu Leu Ala Arg Asp Ser Ile Tyr Tyr Val Asp Ala Asn Ala
1               5                   10                  15
```

<210> SEQ ID NO 15
<211> LENGTH: 13
<212> TYPE: PRT
<213> ORGANISM: Mycobacterium tuberculosis

<400> SEQUENCE: 15

```
Arg Asp Ser Ile Tyr Tyr Val Asp Ala Asn Ala Ser Ile
1               5                   10
```

<210> SEQ ID NO 16
<211> LENGTH: 15
<212> TYPE: PRT
<213> ORGANISM: Mycobacterium tuberculosis

<400> SEQUENCE: 16

```
Ser Ile Tyr Tyr Val Asp Ala Asn Ala Ser Ile Gln Glu Met Leu
1               5                   10                  15
```

<210> SEQ ID NO 17
<211> LENGTH: 14
<212> TYPE: PRT
<213> ORGANISM: Mycobacterium tuberculosis

<400> SEQUENCE: 17

```
Val Asp Ala Asn Ala Ser Ile Gln Glu Met Leu Asn Val Met
1               5                   10
```

<210> SEQ ID NO 18
<211> LENGTH: 13
<212> TYPE: PRT
<213> ORGANISM: Mycobacterium tuberculosis

<400> SEQUENCE: 18

```
Val Gly Ile Val Thr Glu Ala Asp Ile Ala Arg His Leu
1               5                   10
```

<210> SEQ ID NO 19
<211> LENGTH: 15
<212> TYPE: PRT
<213> ORGANISM: Mycobacterium tuberculosis

<400> SEQUENCE: 19

```
Ile Val Thr Glu Ala Asp Ile Ala Arg His Leu Pro Glu His Ala
1               5                   10                  15
```

<210> SEQ ID NO 20
<211> LENGTH: 15
<212> TYPE: PRT
<213> ORGANISM: Mycobacterium tuberculosis

<400> SEQUENCE: 20

```
Ala Asp Ile Ala Arg His Leu Pro Glu His Ala Ile Val Gln Phe
1               5                  10                  15
```

<210> SEQ ID NO 21
<211> LENGTH: 15
<212> TYPE: PRT
<213> ORGANISM: Mycobacterium tuberculosis

<400> SEQUENCE: 21

```
Arg His Leu Pro Glu His Ala Ile Val Gln Phe Val Lys Ala Ile
1               5                  10                  15
```

<210> SEQ ID NO 22
<211> LENGTH: 15
<212> TYPE: PRT
<213> ORGANISM: Mycobacterium tuberculosis

<400> SEQUENCE: 22

```
Glu His Ala Ile Val Gln Phe Val Lys Ala Ile Cys Ser Pro Met
1               5                  10                  15
```

<210> SEQ ID NO 23
<211> LENGTH: 100
<212> TYPE: PRT
<213> ORGANISM: Mycobacterium tuberculosis

<400> SEQUENCE: 23

```
Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100
```

<210> SEQ ID NO 24
<211> LENGTH: 95
<212> TYPE: PRT
<213> ORGANISM: Mycobacterium tuberculosis

<400> SEQUENCE: 24

```
Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
                20                  25                  30

Lys Gln Ser Leu Thr Lys Leu Ala Ala Ala Trp Gly Gly Ser Gly Ser
            35                  40                  45
```

-continued

Glu Ala Tyr Gln Gly Val Gln Gln Lys Trp Asp Ala Thr Ala Thr Glu
            50                  55                  60

Leu Asn Asn Ala Leu Gln Asn Leu Ala Arg Thr Ile Ser Glu Ala Gly
 65                  70                  75                  80

Gln Ala Met Ala Ser Thr Glu Gly Asn Val Thr Gly Met Phe Ala
                 85                  90                  95

<210> SEQ ID NO 25
<211> LENGTH: 15
<212> TYPE: PRT
<213> ORGANISM: Mycobacterium tuberculosis

<400> SEQUENCE: 25

Met Thr Thr Ala Arg Asp Ile Met Asn Ala Gly Val Thr Cys Val
 1               5                  10                  15

<210> SEQ ID NO 26
<211> LENGTH: 14
<212> TYPE: PRT
<213> ORGANISM: Mycobacterium tuberculosis

<400> SEQUENCE: 26

Arg Asp Ile Met Asn Ala Gly Val Thr Cys Val Gly Glu His
 1               5                  10

<210> SEQ ID NO 27
<211> LENGTH: 14
<212> TYPE: PRT
<213> ORGANISM: Mycobacterium tuberculosis

<400> SEQUENCE: 27

Met Asn Ala Gly Val Thr Cys Val Gly Glu His Glu Thr Leu
 1               5                  10

<210> SEQ ID NO 28
<211> LENGTH: 15
<212> TYPE: PRT
<213> ORGANISM: Mycobacterium tuberculosis

<400> SEQUENCE: 28

Gly Val Thr Cys Val Gly Glu His Glu Thr Leu Thr Ala Ala Ala
 1               5                  10                  15

<210> SEQ ID NO 29
<211> LENGTH: 15
<212> TYPE: PRT
<213> ORGANISM: Mycobacterium tuberculosis

<400> SEQUENCE: 29

Val Gly Glu His Glu Thr Leu Thr Ala Ala Ala Gln Tyr Met Arg
 1               5                  10                  15

<210> SEQ ID NO 30
<211> LENGTH: 15
<212> TYPE: PRT
<213> ORGANISM: Mycobacterium tuberculosis

<400> SEQUENCE: 30

His Gly Met Leu Thr Asp Arg Asp Ile Val Ile Lys Gly Leu Ala
 1               5                  10                  15

<210> SEQ ID NO 31
<211> LENGTH: 14
<212> TYPE: PRT

<213> ORGANISM: Mycobacterium tuberculosis

<400> SEQUENCE: 31

Thr Asp Arg Asp Ile Val Ile Lys Gly Leu Ala Ala Gly Leu
1               5                   10

<210> SEQ ID NO 32
<211> LENGTH: 16
<212> TYPE: PRT
<213> ORGANISM: Mycobacterium tuberculosis

<400> SEQUENCE: 32

Asp Ile Val Ile Lys Gly Leu Ala Ala Gly Leu Asp Pro Asn Thr Ala
1               5                   10                  15

<210> SEQ ID NO 33
<211> LENGTH: 13
<212> TYPE: PRT
<213> ORGANISM: Mycobacterium tuberculosis

<400> SEQUENCE: 33

Gly Leu Ala Ala Gly Leu Asp Pro Asn Thr Ala Thr Ala
1               5                   10

<210> SEQ ID NO 34
<211> LENGTH: 15
<212> TYPE: PRT
<213> ORGANISM: Mycobacterium tuberculosis

<400> SEQUENCE: 34

Ala Ala Gly Leu Asp Pro Asn Thr Ala Thr Ala Gly Glu Leu Ala
1               5                   10                  15

<210> SEQ ID NO 35
<211> LENGTH: 15
<212> TYPE: PRT
<213> ORGANISM: Mycobacterium tuberculosis

<400> SEQUENCE: 35

Ile Gln Glu Met Leu Asn Val Met Glu Glu His Gln Val Arg Arg
1               5                   10                  15

<210> SEQ ID NO 36
<211> LENGTH: 15
<212> TYPE: PRT
<213> ORGANISM: Mycobacterium tuberculosis

<400> SEQUENCE: 36

Leu Asn Val Met Glu Glu His Gln Val Arg Arg Val Pro Val Ile
1               5                   10                  15

<210> SEQ ID NO 37
<211> LENGTH: 15
<212> TYPE: PRT
<213> ORGANISM: Mycobacterium tuberculosis

<400> SEQUENCE: 37

Glu Glu His Gln Val Arg Arg Val Pro Val Ile Ser Glu His Arg
1               5                   10                  15

<210> SEQ ID NO 38
<211> LENGTH: 15
<212> TYPE: PRT
<213> ORGANISM: Mycobacterium tuberculosis

```
<400> SEQUENCE: 38

Val Arg Arg Val Pro Val Ile Ser Glu His Arg Leu Val Gly Ile
1               5                   10                  15

<210> SEQ ID NO 39
<211> LENGTH: 15
<212> TYPE: PRT
<213> ORGANISM: Mycobacterium tuberculosis

<400> SEQUENCE: 39

Pro Val Ile Ser Glu His Arg Leu Val Gly Ile Val Thr Glu Ala
1               5                   10                  15

<210> SEQ ID NO 40
<211> LENGTH: 20
<212> TYPE: PRT
<213> ORGANISM: Mycobacterium tuberculosis

<400> SEQUENCE: 40

Leu Thr Ala Ala Ala Gln Tyr Met Arg Glu His Asp Ile Gly Ala Leu
1               5                   10                  15

Pro Ile Cys Gly
            20

<210> SEQ ID NO 41
<211> LENGTH: 20
<212> TYPE: PRT
<213> ORGANISM: Mycobacterium tuberculosis

<400> SEQUENCE: 41

Gly Glu Leu Ala Arg Asp Ser Ile Tyr Tyr Val Asp Ala Asn Ala Ser
1               5                   10                  15

Ile Gln Glu Met
            20

<210> SEQ ID NO 42
<211> LENGTH: 20
<212> TYPE: PRT
<213> ORGANISM: Mycobacterium tuberculosis

<400> SEQUENCE: 42

Arg His Leu Pro Glu His Ala Ile Val Gln Phe Val Lys Ala Ile Cys
1               5                   10                  15

Ser Pro Met Ala
            20
```

COMPOSITIONS USEFUL IN THE
DIAGNOSTIC OF LATENTLY INFECTED
*MYCOBACTERIUM TUBERCULOSIS*

CROSS REFERENCE TO RELATED
APPLICATIONS

This application is continuation of U.S. application Ser. No. 15/505,292, now U.S. Pat. No. 10,067,147, filed Feb. 21, 2017 which was a National Stage Application based on the International Application No. PCT/EP2015/069791 filed Aug. 28, 2015 which claims priority to European Application 14306329.5 filed Aug. 29, 2014.

The present invention concerns a composition comprising at least three peptides derived from *Mycobacterium tuberculosis* antigen Rv2626c, its use in the diagnostic of latently infected *Mycobacterium tuberculosis* (LTBI) subjects, corresponding methods of use and kits.

BACKGROUND

Despite the availability of anti-*tuberculosis* therapy during the last five decades, the disease caused by *M. tuberculosis* continues to be one of the most prevalent infectious diseases worldwide. Accordingly, in 2011, nearly 9 million new cases of *tuberculosis* (TB) and 1.4 million deaths were reported. In addition, the World Health Organization has estimated that one third of the world population would be infected with latent *M. tuberculosis* (LTBI), a condition where individuals are infected by the intracellular bacteria without exhibiting active disease but with a high risk of reactivation. Primary infection leads to active *tuberculosis* in less than 10% of infected individuals, while in the majority of the cases the immune system is able to contain, but not eliminate, the infection, leading to LTBI. Latency can persist throughout lifetime, but weakness of the immune response of the host can lead to reactivation.

Latent *tuberculosis* can lead to active disease in case of immunodepression, which can be due to therapeutical treatments (for autoimmune diseases such as rheumatoid arthritis or for organ transplantation), malnutrition or old age. The situation is aggravated by the high rate of *M. tuberculosis*-HIV co-infection, since AIDS leads to immunosuppression and therefore to *tuberculosis* activation.

The existence of such a huge reservoir of the pathogen (almost 2 billion people) requires an urgent sensitive and early diagnosis of *tuberculosis* infection in order to control active disease. Knowing if an individual is latently infected can change treatment decision, as in the case of an organ transplant which requires an immunosuppressive treatment.

Interferon gamma release assays (IGRAs) represent the most novel *tuberculosis* infection diagnostic assays and, despite their limitations, have been well received in most developed countries. While the *M. tuberculosis* antigens CFP-10 and ESAT-6 are currently being used for such diagnosis, they are not able to discriminate active and latent infection.

The lack of a gold standard for diagnosing LTBI has thus remained a main hurdle. Indeed, the identification of these subjects by sensitive and fast diagnostic tests represents a crucial aim for the eradication of *tuberculosis* disease and the currently available tests are not sensitive enough, being unable to differentiate between latent and active infected individuals.

The aim of this invention was thus to identify new antigens that would allow to specifically discriminate latently infected individuals from healthy controls and patients with active *tuberculosis*, which the currently available tests are unable to do.

A further aim was to allow a single test to discriminate among the three groups of subjects (LTBI, TB patients and healthy patients). Such test would eliminate the need of radiological and clinical data to differentiate between active and latently infected individuals.

DESCRIPTION OF THE INVENTION

The present invention relates to a mixture of peptides derived from the *M. tuberculosis* antigen Rv2626c that, unlike current commercial tests, discriminates LTBI individuals from patients with *tuberculosis* active disease and from healthy subjects.

In addition, the present invention also relates to a combination of these peptides with the antigens CFP-10 and ESAT-6 (which only discriminate *M. tuberculosis* infection, either latent or active) this combination being able, in one test, to discriminate between the three groups of individuals: healthy subjects, individuals with latent infection and patients with active disease.

The invention thus relates to a composition comprising at least two peptides, in which the amino acid sequences of said at least two peptides consist of distinctive fragments of from 3 to 30 contiguous amino acids of the amino acid sequence of *Mycobacterium tuberculosis* antigen Rv2626c of SEQ ID No 1 (MTTARDIMNAGVTCVGEHETLTAAAQYMREHDIGALPICGDDDRLHGMLTDRDIVIKGLA AGLDPNTATAGELARDSIYYVDANASIQEMLNVMEEHQVRRVPVISEHRLVGIVTEADIA RHLPEHAIVQFVKAICSPMALAS).

More precisely, the present invention relates to a composition comprising at least three peptides, in which the amino acid sequences of said at least three peptides consist of distinctive fragments of from 5 to 30 contiguous amino acids of the amino acid sequence of *Mycobacterium tuberculosis* antigen Rv2626c of SEQ ID No 1, the peptides of the amino acid sequence of SEQ ID No 40 (LTAAAQYMREHDIGALPICG), SEQ ID No 41 (GELARDSIYYVDANASIQEM) and SEQ ID No 42 (RHLPEHAIVQFVKAICSPMA) being excluded.

In the scope of the invention, the term "composition" can be used interchangeably with the term "combination product", the term "combination product" covering pools of peptides i.e. mixture of peptides of at least three peptides as described in the present invention.

In the scope of the present invention, the peptides of SEQ ID No 40, SEQ ID No 41 and SEQ ID No 42, as above mentioned, are not part of the composition described herein.

*Mycobacterium tuberculosis* antigen Rv2626c is a dormancy induced *Mycobacterium* protein and related information can be found at hypertext transfer protocol://tuberculist.epfl.ch/index.html.

In particular, the composition according to the invention comprises between 2 and 10 peptides, more particularly between 3 and 10 peptides, for example 3, 4, 5, 6, 7, 8, 9 or 10 peptides, and even more particularly 6 peptides.

In particular, the at least two or three peptides, preferably the at least three peptides, consist of distinctive fragments of from 5 to 20 contiguous amino acids, or from 10 to 30 contiguous amino acids, more particularly from 12 to 20 contiguous amino acids, even more particularly from 13 to 17 or 13 to 15 contiguous amino acids, and for example of 10, 11, 12, 13, 14, 15, 16, 17, 18, 19 or 20, and preferably 13, 14, 15, 16 or 17 contiguous amino acids of the amino acid sequence of *Mycobacterium tuberculosis* antigen Rv2626c of SEQ ID No 1. Said at least two or three peptides, preferably said at least three peptides, can have the same sequence length or a different one. In particular, said peptides can have sequences that overlap by at least 3 amino acids, more particularly by at least 10 amino acids and for example by 11 amino acids.

In one embodiment, the amino acid sequences of said at least three peptides thus comprise distinctive fragments of from 10 to 30 contiguous amino acids, preferably from 12 to 20 contiguous amino acids of the amino acid sequence of *Mycobacterium tuberculosis* antigen Rv2626c of SEQ ID No 1.

In one embodiment, the amino acid sequences of said at least two or three peptides, preferably said at least three peptides, do not comprise the C-terminal amino acids G, P, E, D, Q, N, T or S and/or the N-terminal amino acid Q. Said at least two or three peptides, preferably said at least three peptides, can for example be chosen among:

peptide 6 of SEQ ID No 2 (etltaaaqymrehdi);
peptide 12 of SEQ ID No 3 (ddrlhgmltdrdivi);
peptide 18 of SEQ ID No 4 (dpntatagelardsi);
peptide 24 of SEQ ID No 5 (nasiqemlnvmeeh);
peptide 30 of SEQ ID No 6 (ehrlvgivteadiar);
peptide 36 of SEQ ID No 7 (vqfvkaicspmalas);
peptide 7 of SEQ ID No 8 (aaaqymrehdigal);
peptide 8 of SEQ ID No 9 (aqymrehdigalpi);
peptide 9 of SEQ ID No 10 (mrehdigalpicgdddr);
peptide 10 of SEQ ID No 11 (galpicgdddrlhgm);
peptide 11 of SEQ ID No 12 (icgdddrlhgmltdr);
peptide 19 of SEQ ID No 13 (atagelardsiyyv);
peptide 20 of SEQ ID No 14 (gelardsiyyvdana);
peptide 21 of SEQ ID No 15 (rdsiyyvdanasi);
peptide 22 of SEQ ID No 16 (siyyvdanasiqeml);
peptide 23 of SEQ ID No 17 (vdanasiqemlnvm);
peptide 31 of SEQ ID No 18 (vgivteadiarhl);
peptide 32 of SEQ ID No 19 (ivteadiarhlpeha);
peptide 33 of SEQ ID No 20 (adiarhlpehaivqf);
peptide 34 of SEQ ID No 21 (rhlpehaivqfvkai);
peptide 35 of SEQ ID No 22 (ehaivqfvkaicspm);
peptide 1 of SEQ ID No 25 (mttardimnagvtcv);
peptide 2 of SEQ ID No 26 (rdimnagvtcvgeh);
peptide 3 of SEQ ID No 27 (mnagvtcvgehetl);
peptide 4 of SEQ ID No 28 (gvtcvgehetltaaa);
peptide 5 of SEQ ID No 29 (vgehetltaaaqymr);
peptide 13 of SEQ ID No 30 (hgmltdrdivikgla);
peptide 14 of SEQ ID No 31 (tdrdivikglaagl);
peptide 15 of SEQ ID No 32 (divikglaagldpnta);
peptide 16 of SEQ ID No 33 (glaagldpntata);
peptide 17 of SEQ ID No 34 (aagldpntatagela);
peptide 25 of SEQ ID No 35 (iqemlnvmeehqvrr);
peptide 26 of SEQ ID No 36 (Invmeehqvrrvpvi);
peptide 27 of SEQ ID No 37 (eehqvrrvpvisehr);
peptide 28 of SEQ ID No 38 (vrrvpvisehrlvgi);
and
peptide 29 of SEQ ID No 39 (pvisehrlvgivtea).

In one embodiment, the composition according to the invention does not comprise more than two peptides chosen from peptides 1, 2, 3, 4, 5, 6, 25, 26, 27, 28, 29 and 30.

Said at least two or three peptides, preferably said at least three peptides, can also be chosen among distinctive fragments of the above mentioned peptides 6, 12, 18, 24, 30, 36, 7, 8, 9, 10, 11, 19, 20, 21, 22, 23, 31, 32, 33, 34, 35, 1, 2, 3, 4, 5, 13, 14, 15, 16, 17, 25, 26, 27, 28 and 29, in particular fragments of at least 3 amino acids thereof, more particularly fragments of 4, 5, 6, 7, 8, 9 or 10 amino acids thereof.

Said at least two or three peptides, preferably said at least three peptides, can also be chosen among peptides with amino acid sequences more than 70% identical, at least 80% or at least 90% and more particularly at least 91%, 92%, 93%, 94%, 95%, 96%, 97%, 98% or 99% identical to the amino sequences of peptides 6, 12, 18, 24, 30, 36, 7, 8, 9, 10, 11, 19, 20, 21, 22, 23, 31, 32, 33, 34, 35, 1, 2, 3, 4, 5, 13, 14, 15, 16, 17, 25, 26, 27, 28 and 29 mentioned above.

Such variants include allelic variants and the deletion, modification, or addition of single amino acids or groups of amino acids within the peptide sequence, as long as the peptide maintains the ability to diagnose LTBI subjects and as long as its length is from 3 to 30 amino acids, preferably from 5 to 30 amino acids.

The at least two or three peptides of the composition of the invention, preferably the at least three peptides of the composition of the invention, may be chemically modified, for example post-transationally modified. For example, they can be glycosylated or comprise modified amino acids residues. They may be also modified by the addition of histidine residues to assist their purification.

In one embodiment, said at least three peptides are thus chosen from:

peptide 6 of SEQ ID No 2 or a fragment of at least 3 amino acids thereof;
peptide 12 of SEQ ID No 3 or a fragment of at least 3 amino acids thereof;
peptide 18 of SEQ ID No 4 or a fragment of at least 3 amino acids thereof;
peptide 24 of SEQ ID No 5 or a fragment of at least 3 amino acids thereof;
peptide 30 of SEQ ID No 6 or a fragment of at least 3 amino acids thereof;
peptide 36 of SEQ ID No 7 or a fragment of at least 3 amino acids thereof;
peptide 7 of SEQ ID No 8 or a fragment of at least 3 amino acids thereof;
peptide 8 of SEQ ID No 9 or a fragment of at least 3 amino acids thereof;
peptide 9 of SEQ ID No 10 or a fragment of at least 3 amino acids thereof;
peptide 10 of SEQ ID No 11 or a fragment of at least 3 amino acids thereof;
peptide 11 of SEQ ID No 12 or a fragment of at least 3 amino acids thereof;
peptide 19 of SEQ ID No 13 or a fragment of at least 3 amino acids thereof;
peptide 20 of SEQ ID No 14 or a fragment of at least 3 amino acids thereof;
peptide 21 of SEQ ID No 15 or a fragment of at least 3 amino acids thereof;
peptide 22 of SEQ ID No 16 or a fragment of at least 3 amino acids thereof;
peptide 23 of SEQ ID No 17 or a fragment of at least 3 amino acids thereof;
peptide 31 of SEQ ID No 18 or a fragment of at least 3 amino acids thereof;
peptide 32 of SEQ ID No 9 or a fragment of at least 3 amino acids thereof;
peptide 33 of SEQ ID No 20 or a fragment of at least 3 amino acids thereof;
peptide 34 of SEQ ID No 21 or a fragment of at least 3 amino acids thereof;
peptide 35 of SEQ ID No 22 or a fragment of at least 3 amino acids thereof;
peptide 1 of SEQ ID No 25 or a fragment of at least 3 amino acids thereof;

peptide 2 of SEQ ID No 26 or a fragment of at least 3 amino acids thereof;
peptide 3 of SEQ ID No 27 or a fragment of at least 3 amino acids thereof;
peptide 4 of SEQ ID No 28 or a fragment of at least 3 amino acids thereof;
peptide 5 of SEQ ID No 29 or a fragment of at least 3 amino acids thereof;
peptide 13 of SEQ ID No 30 or a fragment of at least 3 amino acids thereof;
peptide 14 of SEQ ID No 31 or a fragment of at least 3 amino acids thereof;
peptide 15 of SEQ ID No 32 or a fragment of at least 3 amino acids thereof;
peptide 16 of SEQ ID No 33 or a fragment of at least 3 amino acids thereof;
peptide 17 of SEQ ID No 34 or a fragment of at least 3 amino acids thereof;
peptide 25 of SEQ ID No 35 or a fragment of at least 3 amino acids thereof;
peptide 26 of SEQ ID No 36 or a fragment of at least 3 amino acids thereof;
peptide 27 of SEQ ID No 37 or a fragment of at least 3 amino acids thereof;
peptide 28 of SEQ ID No 38 or a fragment of at least 3 amino acids thereof; and
peptide 29 of SEQ ID No 39 or a fragment of at least 3 amino acids thereof.

In another embodiment, said at least three peptides are chosen from:
peptides 6, 12 and 18, or fragments of at least 3 amino acids thereof;
peptides 6, 12 and 24, or fragments of at least 3 amino acids thereof;
peptides 6, 12 and 30, or fragments of at least 3 amino acids thereof;
peptides 6, 12 and 36, or fragments of at least 3 amino acids thereof;
peptides 6, 18 and 24, or fragments of at least 3 amino acids thereof;
peptides 6, 18 and 30, or fragments of at least 3 amino acids thereof;
peptides 6, 18 and 36, or fragments of at least 3 amino acids thereof;
peptides 6, 24 and 30, or fragments of at least 3 amino acids thereof;
peptides 6, 24 and 36, or fragments of at least 3 amino acids thereof;
peptides 6, 30 and 36, or fragments of at least 3 amino acids thereof;
peptides 7, 8 and 9, or fragments of at least 3 amino acids thereof;
peptides 7, 8 and 10, or fragments of at least 3 amino acids thereof;
peptides 7, 8 and 11, or fragments of at least 3 amino acids thereof;
peptides 7, 8 and 12, or fragments of at least 3 amino acids thereof;
peptides 7, 9 and 10, or fragments of at least 3 amino acids thereof;
peptides 7, 9 and 11, or fragments of at least 3 amino acids thereof;
peptides 7, 8 and 12, or fragments of at least 3 amino acids thereof;
peptides 7, 10 and 11, or fragments of at least 3 amino acids thereof;
peptides 7, 10 and 12, or fragments of at least 3 amino acids thereof;
peptides 7, 11 and 12, or fragments of at least 3 amino acids thereof;
peptides 13, 14 and 15, or fragments of at least 3 amino acids thereof;
peptides 13, 14 and 16, or fragments of at least 3 amino acids thereof;
peptides 13, 14 and 17, or fragments of at least 3 amino acids thereof;
peptides 13, 14 and 18, or fragments of at least 3 amino acids thereof;
peptides 13, 15 and 16, or fragments of at least 3 amino acids thereof;
peptides 13, 15 and 17, or fragments of at least 3 amino acids thereof;
peptides 13, 15 and 18, or fragments of at least 3 amino acids thereof;
peptides 13, 16 and 17, or fragments of at least 3 amino acids thereof;
peptides 13, 16 and 18, or fragments of at least 3 amino acids thereof;
peptides 13, 17 and 18, or fragments of at least 3 amino acids thereof;
peptides 19, 20 and 21, or fragments of at least 3 amino acids thereof;
peptides 19, 20 and 22, or fragments of at least 3 amino acids thereof;
peptides 19, 20 and 23, or fragments of at least 3 amino acids thereof;
peptides 19, 20 and 24, or fragments of at least 3 amino acids thereof;
peptides 19, 21 and 22, or fragments of at least 3 amino acids thereof;
peptides 19, 21 and 23, or fragments of at least 3 amino acids thereof;
peptides 19, 21 and 24, or fragments of at least 3 amino acids thereof;
peptides 19, 22 and 23, or fragments of at least 3 amino acids thereof;
peptides 19, 22 and 24, or fragments of at least 3 amino acids thereof;
peptides 19, 23 and 24, or fragments of at least 3 amino acids thereof;
peptides 31, 32 and 33, or fragments of at least 3 amino acids thereof;
peptides 31, 32 and 34, or fragments of at least 3 amino acids thereof;
peptides 31, 32 and 35, or fragments of at least 3 amino acids thereof;
peptides 31, 32 and 36, or fragments of at least 3 amino acids thereof;
peptides 32, 33 and 34, or fragments of at least 3 amino acids thereof;
peptides 32, 33 and 35, or fragments of at least 3 amino acids thereof;
peptides 32, 33 and 36, or fragments of at least 3 amino acids thereof;
peptides 32, 34 and 35, or fragments of at least 3 amino acids thereof;
peptides 32, 34 and 36, or fragments of at least 3 amino acids thereof;
peptides 32, 35 and 36, or fragments of at least 3 amino acids thereof;
peptides 1, 7 and 13, or fragments of at least 3 amino acids thereof;

peptides 1, 7 and 19, or fragments of at least 3 amino acids thereof;
peptides 1, 7 and 25, or fragments of at least 3 amino acids thereof;
peptides 1, 7 and 31, or fragments of at least 3 amino acids thereof;
peptides 1, 13 and 19, or fragments of at least 3 amino acids thereof;
peptides 1, 13 and 25, or fragments of at least 3 amino acids thereof;
peptides 1, 13 and 31, or fragments of at least 3 amino acids thereof;
peptides 1, 19 and 25, or fragments of at least 3 amino acids thereof;
peptides 1, 19 and 31, or fragments of at least 3 amino acids thereof;
peptides 1, 25 and 31, or fragments of at least 3 amino acids thereof;
peptides 2, 8 and 14, or fragments of at least 3 amino acids thereof;
peptides 2, 8 and 20, or fragments of at least 3 amino acids thereof;
peptides 2, 8 and 26, or fragments of at least 3 amino acids thereof;
peptides 2, 8 and 32, or fragments of at least 3 amino acids thereof;
peptides 2, 14 and 20, or fragments of at least 3 amino acids thereof;
peptides 2, 14 and 26, or fragments of at least 3 amino acids thereof;
peptides 2, 14 and 32, or fragments of at least 3 amino acids thereof;
peptides 2, 20 and 26, or fragments of at least 3 amino acids thereof;
peptides 2, 20 and 32, or fragments of at least 3 amino acids thereof;
peptides 2, 26 and 32, or fragments of at least 3 amino acids thereof;
peptides 3, 9 and 15, or fragments of at least 3 amino acids thereof;
peptides 3, 9 and 21, or fragments of at least 3 amino acids thereof;
peptides 3, 9 and 27, or fragments of at least 3 amino acids thereof;
peptides 3, 9 and 33, or fragments of at least 3 amino acids thereof;
peptides 3, 15 and 21, or fragments of at least 3 amino acids thereof;
peptides 3, 15 and 27, or fragments of at least 3 amino acids thereof;
peptides 3, 15 and 33, or fragments of at least 3 amino acids thereof;
peptides 3, 21 and 27, or fragments of at least 3 amino acids thereof;
peptides 3, 21 and 33, or fragments of at least 3 amino acids thereof;
peptides 3, 27 and 33, or fragments of at least 3 amino acids thereof;
peptides 4, 10 and 16, or fragments of at least 3 amino acids thereof;
peptides 4, 10 and 22, or fragments of at least 3 amino acids thereof;
peptides 4, 10 and 28, or fragments of at least 3 amino acids thereof;
peptides 4, 10 and 34, or fragments of at least 3 amino acids thereof;
peptides 4, 16 and 22, or fragments of at least 3 amino acids thereof;
peptides 4, 16 and 28, or fragments of at least 3 amino acids thereof;
peptides 4, 16 and 34, or fragments of at least 3 amino acids thereof;
peptides 4, 22 and 28, or fragments of at least 3 amino acids thereof;
peptides 4, 22 and 34, or fragments of at least 3 amino acids thereof;
peptides 4, 28 and 34, or fragments of at least 3 amino acids thereof;
peptides 5, 11 and 17, or fragments of at least 3 amino acids thereof; and
peptides 5, 11 and 23, or fragments of at least 3 amino acids thereof;
peptides 5, 11 and 29, or fragments of at least 3 amino acids thereof;
peptides 5, 11 and 35, or fragments of at least 3 amino acids thereof;
peptides 5, 17 and 23, or fragments of at least 3 amino acids thereof;
peptides 5, 17 and 29, or fragments of at least 3 amino acids thereof;
peptides 5, 17 and 35, or fragments of at least 3 amino acids thereof;
peptides 5, 23 and 29, or fragments of at least 3 amino acids thereof;
peptides 5, 23 and 35, or fragments of at least 3 amino acids thereof;
peptides 5, 29 and 35, or fragments of at least 3 amino acids thereof.

In a further embodiment, the composition according to the invention comprises six peptides, in which the amino acid sequences of said six peptides consist of distinctive fragments of from 12 to 20 contiguous amino acids.

In a further embodiment, the composition comprises:
peptides 6, 12, 18, 24, 30 and 36 or fragments of at least 3 amino acids thereof;
peptides 7, 8, 9, 10, 11 and 12 or fragments of at least 3 amino acids thereof;
peptides 19, 20, 21, 22, 23 and 24 or fragments of at least 3 amino acids thereof;
peptides 31, 32, 33, 34, 35 and 36 or fragments of at least 3 amino acids thereof;
peptides 1, 7, 13, 19, 25 and 31 or fragments of at least 3 amino acids thereof;
peptides 2, 8, 14, 20, 26 and 32 or fragments of at least 3 amino acids thereof;
peptides 3, 9, 15, 21, 27 and 33 or fragments of at least 3 amino acids thereof;
peptides 4, 10, 16, 22, 28 and 34 or fragments of at least 3 amino acids thereof;
peptides 5, 11, 17, 23, 29 and 35 or fragments of at least 3 amino acids thereof; or
peptides 13, 14, 15, 16, 17 and 18 or fragments of at least 3 amino acids thereof.

In the above mentioned embodiments, when fragments of at least 3 amino acids of the peptides 6, 12, 18, 24, 30, 36, 7, 8, 9, 10, 11, 19, 20, 21, 22, 23, 31, 32, 33, 34, 35, 1, 2, 3, 4, 5, 13, 14, 15, 16, 17, 25, 26, 27, 28 and 29 are part of the composition according to the invention, each of these fragments has a distinctive amino acid sequence. This means that for example, in the case where the composition would comprise fragments of at least 3 amino acids of peptides 19, 20, 21, 22, 23 and 24, each of these six fragments has a distinctive amino acid sequence.

In one embodiment, the composition according to the invention does not comprise:
peptides 1, 2, 3, 4, 5, and 6; or
peptides 25, 26, 27, 28, 29 and 30.

The invention also relates to a composition as mentioned above further comprising CFP-10 and/or ESAT-6 antigens.

CFP-10 antigen also known as ESAT-6-like antigen esxB or secreted antigenic protein MTSA-10 or 10 kDa culture filtrate antigen CFP-10 or Rv3874 is a protein that is encoded by the esxB gene. Information related to this protein of SEQ ID NO: 23 (MAEMKTDAAT-LAQEAGNFERISGDLKTQIDQVESTAGSLQGQWR-GAAGTAAQAAVVRFQEA ANKQKQELDEIST-NIRQAGVQYSRADEEQQQALSSQMGF) can be found at hypertext transfer protocol://tuberculist.epfl.ch/index.html.

ESAT-6 antigen also known as 6 kDa early secretory antigenic target of *Mycobacterium tuberculosis* or Rv3875, is a secretory protein and potent T cell antigen. Information related to this protein of SEQ ID NO: 24 (MTEQQWNF-AGIEAAASAIQGNVTSIHSLLDEGKQSLTK-LAAAWGGSGSEAYQG VQQKWDATATELNNALQN-LARTISEAGQAMASTEGNVTGMFA) can be found at hypertext transfer protocol://tuberculist.epfl.ch/index.html. The protein is used in tuberculosis diagnosis by the whole blood interferon gamma test QuantiFERON-TB Gold, in conjunction with CFP-10 and TB7.7.

The at least two or three peptides, in particular the at least three peptides, and/or the above mentioned CFP-10 and ESAT-6 antigens of the composition of the invention may be mixed with carriers or diluents which will not interfere with the intended purpose of the peptides and antigens. The composition will generally comprise at least 50%, as for example more than 80%, 90%, 95% or 99%, by weight of the at least two or three peptides, in particular of the at least three peptides.

Routine methods can be employed to synthetize the peptides and the antigens of the compositions according to the invention. Such methods are well known by a man skilled in the art and include techniques such as fmoc synthesis (Mäde et al, Automated solid-phase peptide synthesis to obtain therapeutic peptides Beilstein J Org Chem. 2014; 10: 1197-1212. CFP-10 and ESAT-6 antigens are commercially available.

The invention also relates to a composition as mentioned above for use in the diagnostic of LTBI subjects.

The invention also relates to the use of a composition as mentioned above for the diagnostic of LTBI subjects.

By "LTBI", it is meant latent *tuberculosis* infection or latently infected *Mycobacterium tuberculosis*, a condition where individuals are infected by the intracellular bacteria without exhibiting active disease but with a high risk of reactivation. Primary infection leads to active *tuberculosis* in less than 10% of infected individuals, while in the majority of the cases the immune system is able to contain, but not eliminate, the infection, leading to LTBI. Latency can persist throughout lifetime, but weakness of the immune response of the host (such as HIV infection or any immunosuppressive therapy) can lead to reactivation.

By "subjects", it is meant a human, a male or female, which is afflicted, or has the potential to be afflicted with one or more diseases and conditions described herein.

The invention also relates to a composition as described above which comprises CFP-10 and/or ESAT-6 antigens for use to discriminate between healthy subjects, subjects with active Tuberculosis and LTBI subjects.

The invention also relates to the use of a composition as described above which comprises CFP-10 and/or ESAT-6 antigens, to discriminate between healthy subjects, subjects with active Tuberculosis and LTBI subjects.

By "active Tuberculosis", it is meant a condition wherein the disease is active, that is to say an infectious disease caused usually by *Mycobacterium tuberculosis*. Tuberculosis typically attacks the lungs, but can also affect other parts of the body.

By "healthy subjects", it is meant a subject who has no latent *tuberculosis* infection and no active Tuberculosis.

In particular, the composition for use as mentioned above and/or the use of a composition as mentioned above is in an Interferon Gamma Release Assay (IGRA).

By "Interferon Gamma Release Assay" or "IGRA", it is meant in the context of the invention, a medical test used in the diagnosis of Tuberculosis. Interferon-gamma release assays rely on the fact that T-lymphocytes will release interferon-gamma when exposed to specific antigen.

In particular, the composition for use as mentioned above and/or the use of a composition as mentioned above is to induce IFN-gamma expression.

By "IFN-gamma", it is meant Interferon gamma or IFNγ, a dimerized soluble cytokine that is the only member of the type II class of interferons, known as an immune interferon.

The invention further relates to a method of diagnosing LTBI subjects, said method comprising the use of a composition as mentioned above.

The invention further relates to a method of diagnosing LTBI subjects, said method comprising the use of a composition as mentioned above, by:
(i) measuring the level of expression of IFN-gamma in isolated peripheral blood mononuclear cells (PBMC) or in a blood sample from a subject; and
(ii) deducing therefrom if the subject has a LTBI.

The invention also relates to a method to discriminate between healthy subjects, subjects with active Tuberculosis and LTBI subjects, comprising the use of a composition as described above which comprises CFP-10 and/or ESAT-6 antigens.

The invention also relates to a method to discriminate between healthy subjects, subjects with active Tuberculosis and LTBI subjects comprising the use of a composition as described above which comprises CFP-10 and/or ESAT-6 antigens, by:
(i) measuring the level of expression of IFN-gamma in isolated peripheral blood mononuclear cells (PBMC) or in a blood sample from a subject; and
(ii) deducing therefrom if the subject has a LTBI.

In particular, the above mentioned methods comprise:
(i) culturing isolated peripheral blood mononuclear cells (PBMC) or a blood sample from a subject with a composition as described above;
(ii) measuring the level of expression of IFN-gamma of said isolated peripheral blood mononuclear cells (PBMC) or of said blood sample; and
(iii) deducing therefrom if the subject has a LTBI. In particular, the above mentioned methods are ex vivo methods.

The man skilled in the art is perfectly able to understand what is encompassed by the term "culturing". In particular, by "culturing" is meant to treat, or to incubate either blood sample or PBMC from the subject with the composition according to the invention. For example, the PBMC or blood sample is incubated with the composition according to the invention for example for 24 h or 5 days at 37° C., and then the plasma or supernatant of those cultured samples is recovered, to determine the levels of IFN-gamma in them.

By "blood sample", it is meant a sample which includes whole blood, plasma, serum, circulating epithelial cells, constituents, or any derivative of blood.

The measure of the level of expression of IFN-gamma can be performed by immunoassay or immunoblots or by analytical methods, like for example capillary electrophoresis-mass spectrometry (CE-MS), liquid chromatography coupled to mass spectrometry (LC-MS, LC-MS/MS), quantitative methods with isotopic labeling (stable isotope labeling by amino acids in cell culture (SILAC), isotope coded affinity tags (ICAT), isobaric tag for relative and absolute quantitation (ITRAQ), . . . ), label-free methods like selective reaction monitoring (SRM) or multiple reaction monitoring (MRM) assays, or bio-molecular interaction analysis/surface plasmon resonance (BIA/SPR) technologies encompassing methods with calibration and without calibration as calibration free concentration analysis for example.

The term "immunoassay" as used according to the present invention includes competition, direct reaction, or sandwich type assays. Such assays include, but are not limited to, agglutination test, enzyme-labelled and mediated immunoassays, such as ELISA, biotin/avidin type assay, radioimmunoassay, immunoelectrophoresis, and immunoprecipitation.

These methods are well known by the man skilled in the art.

The invention also relates to a kit for diagnosing LTBI subjects and/or for discriminating healthy subjects, subjects with active Tuberculosis and LTBI subjects comprising:
(i) a composition according to the invention; and
(ii) instructions for use to diagnose LTBI and/or for discriminating healthy subjects, subjects with active *Tuberculosis* and LTBI subjects.

Instructions for using the kit according to the invention may comprise instructions for processing the biological sample obtained from the subject and/or for performing the test, or instructions for interpreting the results. A kit may also contain a notice in the form prescribed by a governmental agency regulating the manufacture, use or sale of pharmaceuticals or biological products.

The kit according to the invention can further comprise means for measuring the level of expression of IFN-gamma.

According to an embodiment, said means can be a specific antibody directed against IFN-gamma.

Such means can be labeled with detectable compound such as fluorophores or radioactive compounds. For example, the antibody specifically binding to said protein may be labeled with a detectable compound. Alternatively, when the kit comprises an antibody, the kit may further comprise a secondary antibody, labeled with a detectable compound, which binds to an unlabeled antibody specifically binding to said protein.

In addition, a kit of the invention can also comprise at least one reagent for the detection of a complex between the means for measuring the expression level of expression of said protein included in the kit and said protein.

Depending on the procedure, the kit may further comprise one or more of: extraction buffer and/or reagents, western blotting buffer and/or reagents, and detection means.

The kits of the present invention may optionally comprise different containers (e.g., vial, ampoule, test tube, flask or bottle) for each individual buffer and/or reagent and/or peptides and/or antigens. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

The invention will be further illustrated by the following figures and examples.

EXAMPLES

Example 1

Protocols

Subjects

Healthy adults lacking a history of *tuberculosis* that had received *Bacillus* Calmette-Guerin (BCG) vaccination at birth participated in the study. Among this group, the diagnosis of latent *tuberculosis* (LTBI subjects) was established using QuantiFERON TB In-tube Gold® test (Cellestis Inc.), following the manufacturer's instructions. This test was used to discriminate LTBI subjects among a healthy population. Indeed, as this test, as already mentioned, does not allow to discriminate active TB subjects from LTBI subjects, it was made sure to analyze a healthy population with no possibility of active TB to be able to conclude that QuantiFERON positive individuals were LTBI subjects.

HIV-uninfected patients with active *tuberculosis* (TB subjects) were evaluated at the Dr. F. Muñiz Hospital, Buenos Aires, Argentina. Diagnosis of disease was established based on clinical and radiological data together with the identification of acid-fast bacilli (AFB) in sputum. Patients included in this study had received less than 1 week of anti-*tuberculosis* therapy.

The control group (HD subjects) included individuals that matched in terms of sex, age and ethnicity with TB patients and LTBI individuals.

All participants provided a written informed consent for the collection of peripheral blood samples and subsequent analysis.

The protocols conducted in this work were approved by the Ethical Committee of the Hospital Muñiz and by the International Review Board Fundación Huésped.

Due to the intensive immigration that Argentina has received from European countries during its history, as well as from other Latin American countries during the last decades, the Argentinean population comprises a very diverse genetic background.

Moreover, since BCG vaccination in mandatory in this country, it is also possible to test if BCG vaccination causes false positives upon stimulation with the compositions according to the invention.

Peptides

Synthetic peptides of 13 to 17 amino acids, spanning the sequence of *Mycobacterium tuberculosis* antigen Rv2626c of SEQ ID No 1 were synthesized by Biomatik Corp. using Fmoc chemistry.

Lyophilized peptides were dissolved in dimethyl sulfoxide (DMSO), aliquoted and stored at −70° C.

Peptide purity was of more than 80%, as assayed by HPLC, and their composition was verified by mass spectrometry.

For in vitro stimulation, 4 pools of 6 peptides were prepared (Table 1), with each peptide at a final concentration of 2 mg/ml, following the methodology previously described by Addo et al (J Virol. 2003 February; 77(3):2081-92).

TABLE 1

*Mycobacterium Tuberculosis* antigen Rv2626c peptides pools

| Pool Reference | Peptide reference | | | | | |
|---|---|---|---|---|---|---|
| 6 | 6 (SEQ ID No 2) | 12 (SEQ ID No 3) | 18 (SEQ ID No 4) | 24 (SEQ ID No 5) | 30 (SEQ ID No 6) | 36 (SEQ ID No 7) |
| 8 | 7 (SEQ ID No 8) | 8 (SEQ ID No 9) | 9 (SEQ ID No 10) | 10 (SEQ ID No 11) | 11 (SEQ ID No 12) | 12 (SEQ ID No 3) |
| 10 | 19 (SEQ ID No 13) | 20 (SEQ ID No 14) | 21 (SEQ ID No 15) | 22 (SEQ ID No 16) | 23 (SEQ ID No 17) | 24 (SEQ ID No 5) |
| 12 | 31 (SEQ ID No 18) | 32 (SEQ ID No 19) | 33 (SEQ ID No 20) | 34 (SEQ ID No 21) | 35 (SEQ ID No 22) | 36 (SEQ ID No 7) |

Cell Preparation and Reagents

Peripheral blood mononuclear cells (PBMC) were isolated by centrifugation over FICOLL-HYPAQUE® (GE Healthcare) and cultured ($1 \times 10^6$ cells/ml) with the different peptide pools (5 μg/ml) with RPMI 1640 (Gibco) supplemented with L-glutamine, penicillin/streptomycin and 10% of human serum (Sigma-Aldrich). After five days, cell free supernatants were collected to determine IFN-γ expression by ELISA (BioLegend).

Results

A pool matrix in which each pool was composed of 6 different peptides was first designed and IFN-γ production against those pools was then tested.

Figure 1:
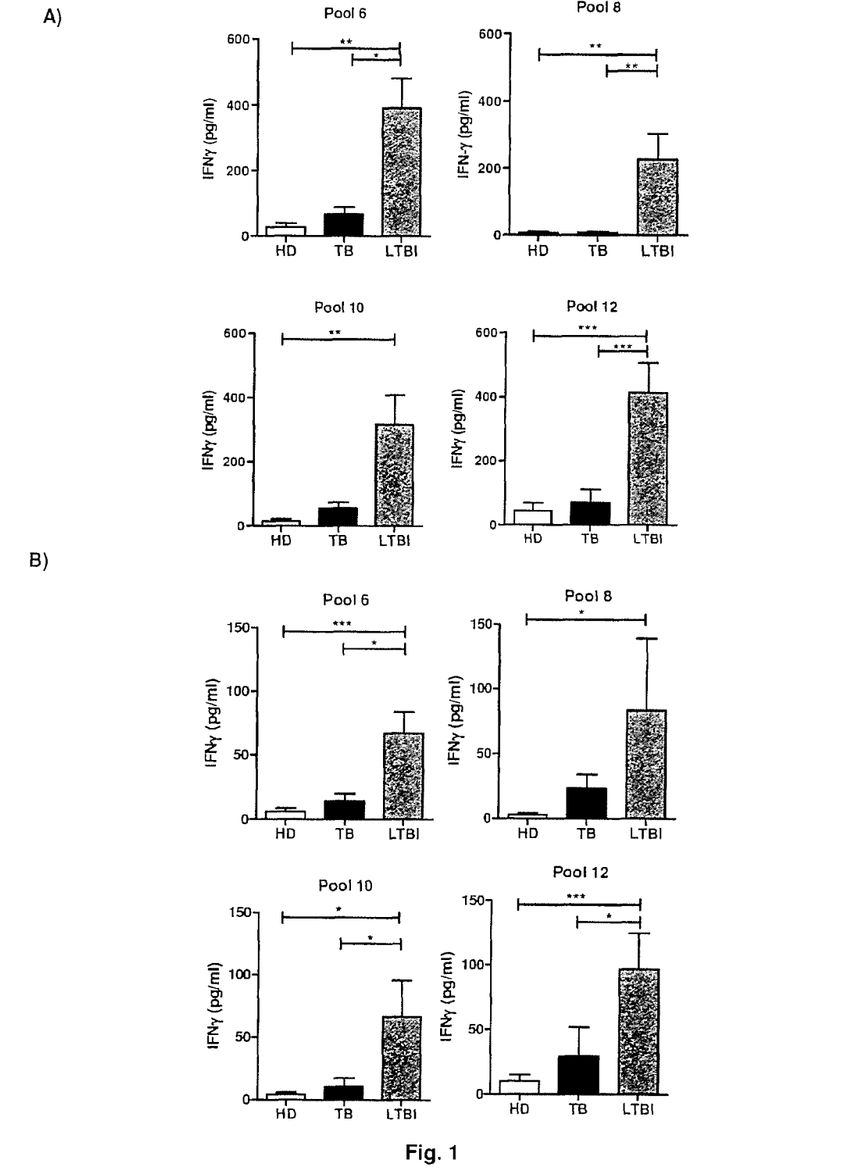
FIGS. 1A and 1B show the IFN-gamma level of expression measured by ELISA on: A) Peripheral blood mononuclear cells (PBMC) from healthy donors (HD), patients with tuberculosis (TB) and latently *M tuberculosis* infected individuals (LTBI) cultured for 5 days with compositions according to the invention and B) Whole blood from healthy donors (HD), patients with tuberculosis (TB) and latently *M tuberculosis* infected individuals (LTBI) cultured for 24H with compositions according to the invention. Bars represent the mean±SEM. Mann-Whitney test for unpaired samples * $p<0.05$,  $p<0.01$, * $p<0.001$.

The results shown in FIGS. 1A and 1B indicate that pools 6, 8, 10 and 12 were able to significantly discriminate LTB1 individuals from patients with tuberculosis and healthy controls by inducing significantly higher levels of IFN-γ in LTBI individuals compared to active TB patients and healthy donors.

These results show that the compositions according to the invention can be used in a diagnostic test to discriminate LTBI subjects among TB, LTBI and HD subjects.

As it was previously mentioned, latent *tuberculosis* infection represents the main reservoir for *M. tuberculosis*, making its effective detection key in the struggle against active disease.

Nowadays, despite their shortcomings, the most commonly used assays for diagnosing latent *tuberculosis* infection are the tuberculin skin test (TST) and two commercial assays: QuantiFERON TB Gold In Tube, from the firm Cellestis GmbH, and T-Spot TB, from the firm Oxford Immunotec. Both commercial kits are interferon gamma release assays (IGRAs), which use specific *M. tuberculosis* peptides (mainly CFP-10 and ESAT-6) to induce secretion of this cytokine in individuals infected with the pathogen.

Thus, while these assays differentiate infected individuals from healthy ones, unlike the compositions according to the invention, they do not discriminate between latent and active infection.

The TST, most commonly used in less developed countries, presents high variability and is dependent on both the observer and the way of administration. It is not standardizable nor objective and, in addition, can present false positives, especially with BCG vaccination. Both T-Spot TB and QuantiFERON TB Gold In Tube assays are much more specific than the TST, however, they are unable to differentiate latently infected individuals from those with active disease.

Table 2 illustrates the expected results using the different available diagnostic tests and the compositions of the invention.

TABLE 2

| Subjects | QuantiFERON TB Gold In Tube | T-Spot TB | TST | Composition of the invention |
|---|---|---|---|---|
| LTBI | + | + | +/− | + |
| TB | + | + | + | − |
| HD | − | −− | +/− | − |

Example 2

Protocols

Subjects.

BCG-vaccinated healthy adults lacking a history of TB (household contacts and healthcare workers) were recruited. Among this group of individuals, diagnosis of LTBI was established using QuantiFERON-TB Gold In-Tube (QFT-GIT; Qiagen, USA; according to manufacturer's directions) and Tuberculin Skin Test (TST) tests. LTBI diagnosis was assigned to any subject with a positive QFT-GIT/TST and no clinical or radiological evidence of active TB. In the event of discordant QFT-GIT/TST results, individuals were assigned to the corresponding group on the basis of the QFT-GIT result. The group of healthy donors (HD) was comprised by adult individuals without TB disease (tested by chest X-rays and analysis of acid-fast bacilli in sputum) and with negative QFT-GIT/TST.

HIV-uninfected patients with active TB were evaluated at Dr. F. Muñiz or Dr. E. Tornú Hospitals (Buenos Aires, Argentina). Diagnosis of TB disease was established based on clinical and radiological data together with culture-confirmation and the identification of acid-fast bacilli in sputum. Patients included in this study had received less than one week of anti-TB therapy.

Information regarding demographic data and prior TB exposure was obtained at the time of recruitment. All participants provided written informed consent for sample collection and subsequent analysis. The protocols conducted were approved by the Ethical Committee of the Dr. F. Muñiz and the Dr. E. Tornú Hospitals and by the International Review Board Fundación Huésped.

Due to the intensive immigration that Argentina has received from European countries during its history, as well as from other Latin American countries during the last decades, the Argentinean population comprises a very diverse genetic background.

als with indeterminate QFT-GIT results were also excluded from the study.

Peptides

Overlapping synthetic peptides (13-17 amino acids, overlapping by 11 amino acids (aa)) spanning the sequence of Rv2626c of SEQ ID No 1 were synthesized by Biomatik Corp. using Fmoc chemistry. Peptide purity was superior to 80%, as assayed by HPLC, and their composition was verified by mass spectrometry. Lyophilized peptides were dissolved in dimethyl sulfoxide (DMSO), aliquoted and stored at −70° C. Table 3 displays the peptide pools used. For in vitro stimulation, peptides were arranged in pools of 6 peptides each (shown in Table 3), with each peptide at a final concentration of 2 mg/ml.

TABLE 3

Mycobacterium Tuberculosis antigen Rv2626c peptides pools

| Pool Reference | Peptide reference | | | | | |
|---|---|---|---|---|---|---|
| 1 | 1 (SEQ ID No 25) | 7 (SEQ ID No 8) | 13 (SEQ ID No 30) | 19 (SEQ ID No 13) | 25 (SEQ ID No 35) | 31 (SEQ ID No 18) |
| 2 | 2 (SEQ ID No 26) | 8 (SEQ ID No 9) | 14 (SEQ ID No 31) | 20 (SEQ ID No 14) | 26 (SEQ ID No 36) | 32 (SEQ ID No 19) |
| 3 | 3 (SEQ ID No 27) | 9 (SEQ ID No 10) | 15 (SEQ ID No 32) | 21 (SEQ ID No 15) | 27 (SEQ ID No 37) | 33 (SEQ ID No 20) |
| 4 | 4 (SEQ ID No 28) | 10 (SEQ ID No 11) | 16 (SEQ ID No 33) | 22 (SEQ ID No 16) | 28 (SEQ ID No 38) | 34 (SEQ ID No 21) |
| 5 | 5 (SEQ ID No 29) | 11 (SEQ ID No 12) | 17 (SEQ ID No 34) | 23 (SEQ ID No 17) | 29 (SEQ ID No 39) | 35 (SEQ ID No 22) |
| 6 | 6 (SEQ ID No 2) | 12 (SEQ ID No 3) | 18 (SEQ ID No 4) | 24 (SEQ ID No 5) | 30 (SEQ ID No 6) | 36 (SEQ ID No 7) |
| 8 | 7 (SEQ ID No 8) | 8 (SEQ ID No 9) | 9 (SEQ ID No 10) | 10 (SEQ ID No 11) | 11 (SEQ ID No 12) | 12 (SEQ ID No 13) |
| 9 | 13 (SEQ ID No 30) | 14 (SEQ ID No 31) | 15 (SEQ ID No 32) | 16 (SEQ ID No 33) | 17 (SEQ ID No 34) | 18 (SEQ ID No 4) |
| 10 | 19 (SEQ ID No 13) | 20 (SEQ ID No 14) | 21 (SEQ ID No 15) | 22 (SEQ ID No 16) | 23 (SEQ ID No 17) | 24 (SEQ ID No 5) |
| 12 | 31 (SEQ ID No 18) | 32 (SEQ ID No 19) | 33 (SEQ ID No 20) | 34 (SEQ ID No 21) | 35 (SEQ ID No 22) | 36 (SEQ ID No 7) |

Moreover, since BCG vaccination in mandatory in this country, it is also possible to test if BCG vaccination causes false positives upon stimulation with the compositions according to the invention.

Study Inclusion and Exclusion Criteria for Individuals Participating in the Study.

Inclusion criteria: a) adult (over 18 years old) men and women with active pulmonary TB and b) healthy volunteers with high level of exposure to M. tuberculosis (household contacts of TB patients and healthcare workers of National Referral Hospitals for TB). All recruited subjects were BCG-vaccinated. QFT-GIT and TST assays were used to determine the presence of LTBI among individuals without clinical or microbiological diagnosis of active TB. All TB patients included in the study had a positive culture for M. tuberculosis.

Exclusion criteria: a) HIV positive or positive serology to other viral or bacterial infections; b) patients with diabetes, cancer, autoimmune diseases or other conditions that may affect the immune system of the individual; c) pregnant women and d) children. Among the population of active TB patients were excluded: a) patients with multidrug-resistant tuberculosis (MDR-TB) infection, b) patients with more than seven consecutive days of anti-TB treatment. Individu- Cell Preparation and Reagents.

Peripheral blood mononuclear cells (PBMC) were isolated by centrifugation over FICOLL-HYPAQUE® (GE Healthcare) and cultured ($1 \times 10^6$ cells/ml) with the different peptide pools (5 µg/ml) with RPMI 1640 (Gibco) supplemented with L-glutamine, penicillin/streptomycin and 10% human serum (Sigma-Aldrich). After five days, cell free supernatants were collected to determine IFN-γ expression by ELISA (BioLegend).

Results

A pool matrix in which each pool was composed of 6 different peptides was first designed and IFN-γ production against those pools was then tested.

Figure 2A:
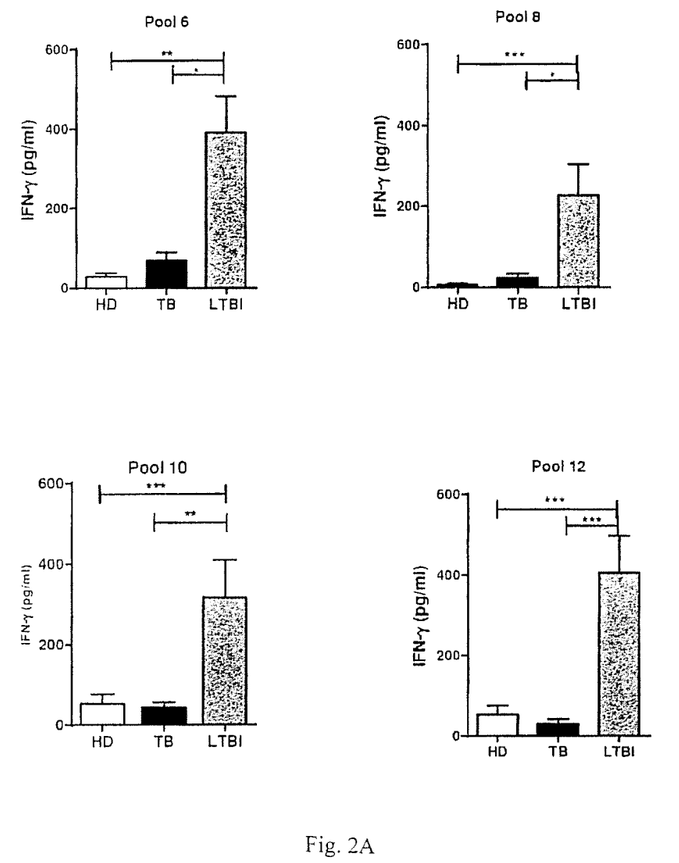
FIGS. 2A and 2B: Peripheral blood mononuclear cells from healthy donors (HD), patients with tuberculosis (TB) and latently *M tuberculosis* infected individuals (LTBI) were cultured with compositions according to the invention. After five days, IFN-γ production was evaluated in cell free supernatants by ELISA. Bars represent the mean±SEM. Mann-Whitney test for unpaired samples * $p<0.05$,  $p<0.01$, * $p<0.001$.
Figure 2B:
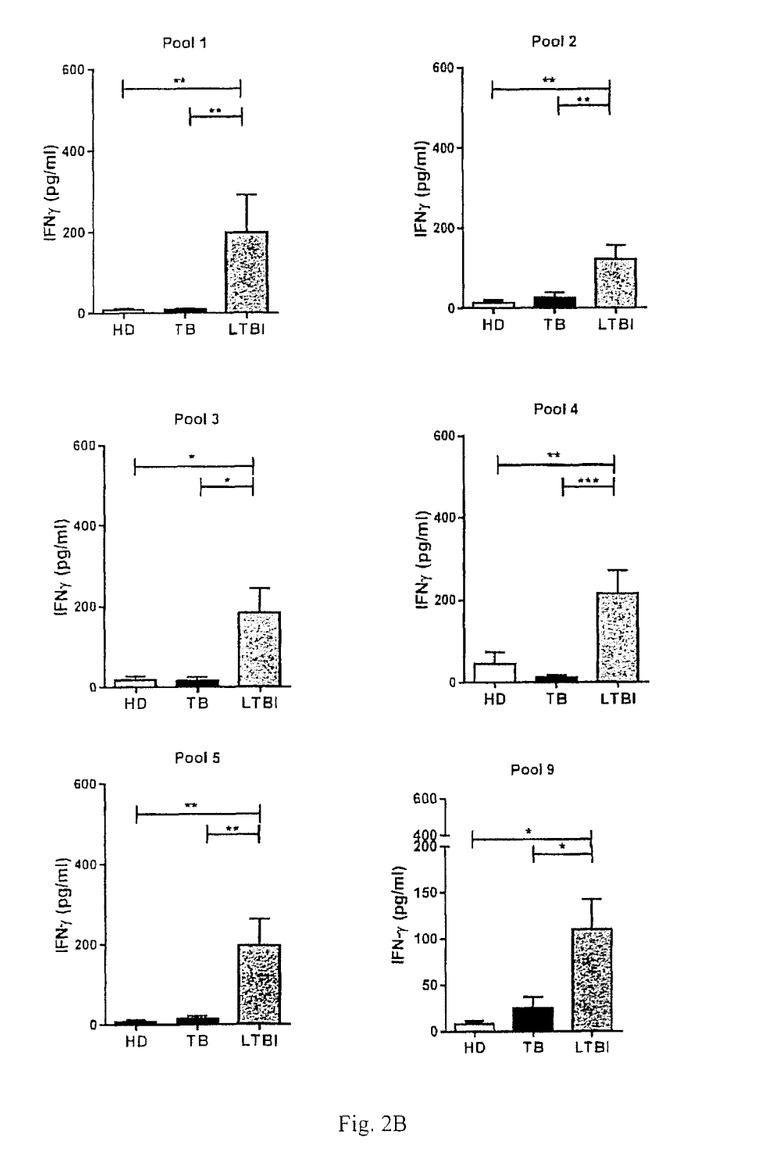

As can be observed in FIGS. 2A and 2B, pools 1, 2, 3, 4, 5, 6, 8, 9, 10 and 12 induced high IFN-γ levels, which significantly discriminate LTB1 individuals from tuberculosis patients and healthy controls.

Taken together these data show that the compositions according to the invention can be used in a diagnostic test to discriminate LTBI subjects among TB, LTBI and HD subjects and are very good candidates to be used in a diagnostic test to discriminate among LTBI subjects from TB patients and HD.

The invention claimed is:

1. A method of diagnosing latently infected *Mycobacterium tuberculosis* (LTBI) in a human subject, said method comprising:
   (i) culturing isolated peripheral blood mononuclear cells (PBMC) or a blood sample from the subject with a composition, wherein the composition comprises peptide 1 consisting of SEQ ID NO: 25, peptide 2 consisting of SEQ ID NO: 26, and peptide 5 consisting of SEQ ID NO: 29; and/or peptide 12 consisting of SEQ ID NO: 3, peptide 23 consisting of SEQ ID NO: 17, and peptide 24 consisting of SEQ ID NO: 5; and
   (ii) measuring the level of expression of IFN-gamma of said cultured PBMC or said cultured blood sample; and
   (iii) diagnosing the LTBI in said human subject when the level of the IFN-gamma in said human subject is higher compared to the level of IFN-gamma in healthy human subjects and human patients with active tuberculosis.

2. A method of discriminating a human subject with LTBI from a healthy human subject and from a human patient with active tuberculosis comprising:
   (i) culturing isolated peripheral blood mononuclear cells (PBMC) or a blood sample from the subject with a composition, wherein the composition comprises peptide 1 consisting of SEQ ID NO: 25, peptide 2 consisting of SEQ ID NO: 26, and peptide 5 consisting of SEQ ID NO: 29;
   and/or peptide 12 consisting of SEQ ID NO: 3, peptide 23 consisting of SEQ ID NO: 17, and peptide 24 consisting of SEQ ID NO: 5, wherein the composition further comprises CFP-10 antigen and/or ESAT antigen of *Mycobacterium tuberculosis*;

(ii) measuring the level of expression of IFN-gamma of said cultured PBMC or said cultured blood sample; and wherein a higher level of the IFN-gamma in said human subject compared to the level of IFN-gamma in the healthy human subject and in the human patient with active tuberculosis discriminates the human subject with LTBI from the healthy human subject and the human patient with active tuberculosis.

\* \* \* \* \*